(12) United States Patent
Schaefer et al.

(10) Patent No.: US 8,479,750 B2
(45) Date of Patent: Jul. 9, 2013

(54) MOUTH CLEANING DEVICE AND HEAD PORTION OF A MOUTH CLEANING DEVICE

(75) Inventors: Norbert Schaefer, Frankfurt am Main (DE); Vladimir Gartstein, Mason, OH (US); Donald james White, Jr., Fairfield, OH (US)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 13/099,512

(22) Filed: May 3, 2011

(65) Prior Publication Data

US 2011/0289699 A1 Dec. 1, 2011

Related U.S. Application Data

(60) Provisional application No. 61/331,967, filed on May 6, 2010.

(51) Int. Cl.
  *A45D 44/18* (2006.01)
(52) U.S. Cl.
  USPC .......................................................... 132/309
(58) Field of Classification Search
  USPC .................. 132/309, 308, 211; 15/110, 111, 15/114, 160, 167.1, 167.2, 176.1, 21.1, 105, 15/4; 604/20; 433/141, 32, 215, 29, 31; 606/161; 601/15, 17
  See application file for complete search history.

(56) References Cited

U.S. PATENT DOCUMENTS

| 4,665,921 | A  | * | 5/1987  | Teranishi et al. | 607/75  |
|-----------|----|---|---------|------------------|---------|
| 5,372,501 | A  | * | 12/1994 | Shalvi           | 433/32  |
| 7,975,341 | B2 | * | 7/2011  | Cai et al.       | 15/22.1 |
| 2006/0010628 | A1 | * | 1/2006 | Moskovich     | 15/111  |
| 2006/0070195 | A1 | * | 4/2006 | Morita et al. | 15/105  |

* cited by examiner

*Primary Examiner* — Todd Manahan
*Assistant Examiner* — Brianne Kalach
(74) *Attorney, Agent, or Firm* — Vladimir Vitenberg; John P. Colbert

(57) ABSTRACT

A head portion for a mouth cleaning device is disclosed. The head portion includes an electrical connecting element; cleaning elements for cleaning teeth; and a tongue cleaning electrode for enabling a current flow into a user's tongue during use. The cleaning elements and the tongue cleaning electrode are arranged on substantially opposing sides of the head portion. The electrical connecting element on the head portion is electrically coupled to the tongue cleaning electrode for establishing an electrical connection with a corresponding electrical connecting element located at a handle portion in a connected state.

11 Claims, 5 Drawing Sheets

MOUTH CLEANING DEVICE AND HEAD PORTION OF A MOUTH CLEANING DEVICE

CROSS REFERENCE TO RELATED APPLICATION

This application claims the benefit of U.S. Provisional Application No. 61/331,967, filed May 6, 2010, the substance of which is incorporated by reference in its entirety herein.

FIELD OF THE INVENTION

The present disclosure relates to a head portion for a mouth cleaning device comprising cleaning elements for cleaning teeth. The present disclosure further relates to a mouth cleaning device comprising such a head portion and a handle. More particularly, the present disclosure relates to mouth cleaning devices that comprise an electrode for additional treatment of the oral cavity by electrophoresis.

BACKGROUND OF THE INVENTION

Halitosis or most commonly bad breath is the result of contamination of the tongue by mostly anaerobic bacteria. When left on the tongue the anaerobic respiration of those bacteria can yield a plurality of bad smells. In order to fight malodour from the tongue it is necessary to clean the bacteria from the tongue. Mints, mouth sprays, mouth wash or gum usually only provide temporary relief as the tongue surface is very rough and the bacteria can hide in the pits and fissures. In order to provide a better cleaning tongue cleaners often also denoted as tongue scrapers are known for collecting and removing the bacterial coating of the tongue. Ergonomic tongue cleaners are shaped in accordance with the anatomy of the tongue, and are optimized to lift and trap the plaque coating and effectively clean the surface of the tongue. There are many different types and designs of tongue cleaners made from plastic, metal or other materials. Most tongue cleaners can generally be described as being spoon-shaped comprising a head portion and a handle portion while having plurality of ribs at their head portion facing towards the tongue for scrubbing the tongue when in operation.

Still the problem remains that a substantial portion of the bacteria stay in the pits and fissures between the papillae of the tongue spreading malodour even after tongue cleaning with known tongue cleaners.

SUMMARY OF THE INVENTION

In one embodiment, a head portion for a mouth cleaning device is provided. The head portion includes an electrical connecting element; cleaning elements for cleaning teeth; and a tongue cleaning electrode for enabling a current flow into a user's tongue during use. The cleaning elements and the tongue cleaning electrode are arranged on substantially opposing sides of the head portion. The electrical connecting element on the head portion is electrically coupled to the tongue cleaning electrode for establishing an electrical connection with a corresponding electrical connecting element located at a handle portion in a connected state.

In another embodiment, a mouth cleaning device is provided. The mouth cleaning device includes a head portion having cleaning elements for cleaning teeth and a tongue cleaning electrode enabling a current flow into a user's tongue in a use state, the cleaning elements and the tongue cleaning electrode being essentially arranged on opposing sides of the head portion; a handle portion having a contact electrode for enabling a current flow into a user's body in a use state; and an energy source. The energy source is electrically coupled to the contact electrode and to the tongue cleaning electrode such that in operation a current may flow from the contact electrode through a user's body to the tongue cleaning electrode.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 1 b) is a cross-sectional cut through the head portion of FIG. 1 a);

DETAILED DESCRIPTION OF THE INVENTION

Figure 1A:
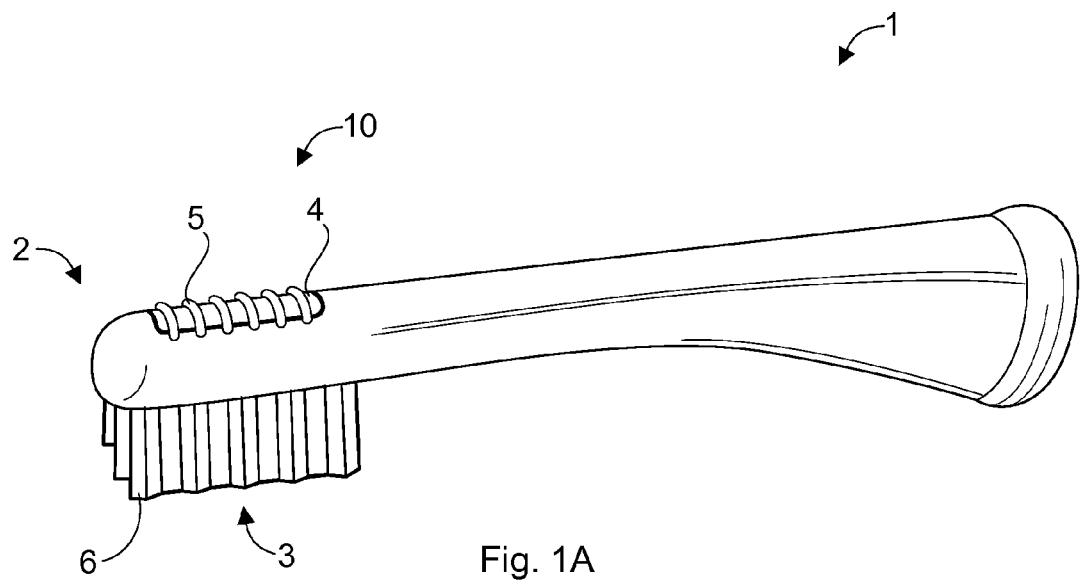
FIG. 1 a) shows a three dimensional drawing of a first embodiment of a head portion for a mouth cleaning device according to an embodiment.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, it is desirable to provide a mouth cleaning device and a head portion for enabling cleaning of a user's tongue in addition to cleaning the user's teeth. According to one embodiment, the head portion includes a plurality of cleaning elements, for example, in the form of bristles arranged in bristle tufts or elastomeric fingers, and a tongue cleaning electrode enabling a current flow into a user's tongue when in use. The tongue cleaning electrode and the cleaning elements are essentially arranged on opposing sides of the head portion such that in use only one of the sides of the head portion will get into contact with the tongue (assuming that the tongue is kept in an essentially flat state). In other words, the tongue cleaning electrode and the cleaning elements face essentially in opposing directions. Further, the head portion comprises an electrical connecting element being electrically coupled to the tongue cleaning electrode for providing an electrical connection with a corresponding electrical connecting element located at a handle portion in an attached state.

According to one embodiment, a mouth cleaning device includes a head portion having a plurality of cleaning elements (for example, as bristles or elastomeric fingers) and a tongue cleaning electrode enabling a current flow into a user's tongue when in use. The tongue cleaning electrode and the cleaning elements are essentially arranged on opposing sides of the head portion such that in use only one of the sides of the head portion will get into contact with the tongue (assuming that the tongue is kept in a flat state). The mouth cleaning device further includes a handle portion having a contact electrode, wherein the contact electrode of the handle portion enables a current flow into a user's hand when in use, and an energy source, wherein the energy source is electrically connected to the contact electrode in the handle portion and to the tongue cleaning electrode in the head portion such that when in operation a current may flow between the contact electrode and the tongue cleaning electrode through a user's body. In one embodiment, the head portion may be an integral (not detachable) part of the mouth cleaning device or it may be a detachable part, in particular to enable replacing the head portion.

The head portion for a mouth cleaning device according to the present disclosure not only enables a mechanical cleaning of the teeth but also an electrically driven cleaning process for the user's tongue based on electrophoresis. The arrangement of the cleaning elements and the tongue cleaning electrode facing at least partly into different directions enables cleaning of the user's teeth as well as the user's tongue without turning the head portion around in the user's mouth, but more prominently, the tongue can be cleaned with a special tongue cleaning side of the toothbrush that may comprise protrusions for mechanically removing debris and bacteria from the tongue in addition to the cleaning action induced by electrophoresis. The arrangement of contact electrode in the handle portion and tongue cleaning electrode in the head portion of the mouth cleaning device allows for providing a current flow from one electrode to the other through the user's body.

The bacteria on the tongue may be fought against by anti-bacterial ions. An anti-bacterial agent comprising the respective anti-bacterial ions can be provided for example as part of a cleaning substance like a dentifrice or mouth rinse, which is applied into the user's mouth. In other embodiments, the anti-bacterial ions can be provided from (ionised) water without addition of an additional anti-bacterial substance or the tongue cleaning electrode may provide anti-bacterial ions, for example, silver ions.

In an embodiment, the cleaning substance or anti-bacterial agent may be provided as an integral part of the mouth cleaning device, for example in a container such as, a gel cushion or a slowly dissolving strip, located next to the tongue cleaning electrode of the head portion.

The polarity of the applied voltage potentials will depend on the charge of the active ions of the anti-bacterial agent in order to provide an effective flow of the anti-bacterial agent into the pits and fissures of the tongue. When, for example, operating with positively charged ions, the tongue cleaning electrode in the head portion of the mouth cleaning device must be positively charged (against the contact electrode) to provide an effective driving of the ions towards the tongue. The current strengths and polarity may be manually adjustable by the user. The current strengths can be reduced to allow the user to become acquainted to the device and later to choose an optimal strength. If a user is very sensitive at the tongue it is possible to reduce the current strengths or if somebody suffers from strong malodour he or she can use a higher strengths of current. The mouth cleaning device may hence be equipped with a respective control element for controlling the polarity of the applied voltages and to control the current strength.

In an embodiment, the applied current is a constant direct current. Alternatively an alternating current or a pulsed current may be used in order to optimize a tongue cleaning. In an embodiment, a periodic change of the polarity of the applied voltage potentials is advantageous. In an embodiment, the handle portion comprises a switch for activating or deactivating the device. In order to restrict the current through the user's body to a physiologically harmless or for the user comfortable level in an embodiment the energy source is arranged such that it limits the current. In an embodiment, the current provided by the energy source through the user's body is in a range from about 20 µA to about 700 µA and in another embodiment between about 50 µA and about 400 µA. In the experience of the inventors, levels over about 80 µA appear to produce unpleasant sensations in users, an electrical feeling and/or sour tastes and in some cases pain. However, the application of increased ionic current levels may be desirable to increase the efficacy of such tongue cleaning devices. Accordingly, tongue cleaning devices that enable increased ionic micro-current levels without causing unpleasant sensations in users of such devices and methods are desired. For example, a ramping current control that increases the level of micro-current from a start current to an end current over a period of time may be used.

In an embodiment, the voltage applied between the electrode ranges from about 8 Volts to about 20 Volts. In particular the applied voltage may have a value of 8 Volts, 10 Volts, 12 Volts, 14 Volts, 16 Volts, 18 Volts or 20 Volts.

In an embodiment, the tongue cleaning electrode includes an electrode area, wherein the electrode area has a surface normal at each point of it, wherein the surface normal of at least one section of the electrode surface and each of the cleaning elements includes an angle of at least about 45°, in another embodiment at least about 70°, and in yet another embodiment at least about 90°. In an embodiment where the cleaning element is an extended element, the angle should be measured between the surface normal and the symmetry axis or longitudinal extension axis of the cleaning element. The electrode area in the sense of the present disclosure is the area covered by the tongue cleaning electrode, wherein the electrode area need not necessarily being entirely electrically conductive, but may be composed for example of a number of alternating conductive surfaces, like blades, ribs or nubs, and isolating sections. Whenever the tongue cleaning electrode comprises a topology or structure the electrode area is the area underlying this structure and determining the overall shape of the electrode. Thus, the surface normal to be considered is the surface normal of the overall electrode area which is not at each point identical to the surface normal of the electrically conductive surface of the tongue cleaning electrode.

This geometric orientation guarantees that the tongue cleaning electrode and the cleaning elements are facing into two different directions enabling an independent cleaning of the user's teeth with the cleaning elements and of the user's tongue with the tongue cleaning electrode. In an embodiment, the surface normal of at least one section of the electrode area of the tongue cleaning electrode and each of the bristles include an angle in a range from about 135° to about 180°. In such an arrangement of the electrode, the tongue cleaning electrode and the cleaning elements are at least partly located opposite each other such that when inserted into the user's oral cavity, the cleaning elements are facing towards the masticatory surface of the user's tooth and the tongue cleaning electrode is facing towards the user's tongue.

In an embodiment, the cleaning elements are arranged to be driven by a mechanical actuator, wherein the mechanical actuator is arranged for establishing connection to an electrical drive providing an electrical toothbrush assembly. In a particular embodiment, the head portion includes a cleaning element carrier that is arranged to provide a rotational oscillatory motion when in use. For such an embodiment of the head portion, the handle portion of the mouth cleaning device includes an electrical drive for connecting to the mechanical actuator in the head portion in order to form an electrical toothbrush.

In another embodiment, the head portion includes a second electrode facing into the first direction (i.e. the direction into which the cleaning elements extend) to enable a current flow into the user's gums or teeth when using the cleaning elements for mechanically cleaning the teeth. In such an embodiment, the ionic tongue cleaning capability of the proposed mouth cleaning device is combined with the known principle of ionic teeth cleaning. In another embodiment, the cleaning elements are at least partly electrically conducting and are thus forming the second electrode.

In yet another embodiment, the second electrode and the tongue cleaning electrode are operated selectively, for example, by providing a control element to selectively switch on only one of the second electrode and tongue cleaning electrode or to switch on both electrodes. The different electrodes may have the same or opposite polarity. The polarity of each of the electrodes may be independently controllable via respective control elements. In an embodiment, the head portion further includes a mechanical tongue cleaning section having a structured surface with at least one protrusion, wherein the mechanical tongue cleaning section is facing into the second direction (i.e. into the direction into which the tongue cleaning electrode is facing). This not only enables an electrically driven cleaning process for the tongue based on electrophoresis but also a mechanical scrubbing of the tongue. The combined mechanical scrubbing together with the effective transport of anti-bacterial agents to the bacteria allows for an improved cleaning of the tongue. In the sense of the present application a rough surface, i.e. like a rasp, is structured and as such comprises a plurality of protrusions.

In a further embodiment, the tongue cleaning electrode is a laminar electrode having an extended contact surface. In an embodiment of the invention, the area over which the mechanical tongue cleaning section extends at least partly overlaps with the area over which the tongue cleaning electrode extends. This guarantees that when mechanically scrubbing the tongue with the mechanical tongue cleaning section of the head portion an electric current can be applied to the tongue simultaneously enabling the above described cleaning process by electrophoresis. In a further embodiment, the mechanical tongue cleaning section and the laminar electrode on the head portion overlap to full extent.

In an embodiment the mechanical cleaning section comprises a plurality of protrusions extending above the electrode. Those protrusions which may have multiple forms of design shall enable an effective scrubbing of the tongue in order to mechanically remove bacteria from the tongue.

Those protrusions in an embodiment may have the shape of ribs, blades or nubs. In pme embodiment, the protrusions provide a rough surface, i.e. like a rasp. The term protrusion in the sense of the present application does exclude filaments, for example filaments used as bristles in a tooth brush. A filament if compared to a protrusion according to the definition used in this application has an additional degree of freedom for flexing. A protrusion on the other hand has the function of following the motion of the carrier and to transmit a significant force for efficient scrapping of the tongue. According to the present disclosure, a significant bending would be disturbing the functionality. A protrusion according to the present disclosure follows the motion of the carrier and allows no or only little internal flexing.

Filaments in toothbrushes made out of Nylon or other plastic materials have typically natural harmonics of 400 to 800 Hz. Those can be calculated by the well known formula:

$$\omega_0 = \sqrt{\frac{E \cdot I \cdot k}{\rho \cdot A \cdot L}},$$

wherein E is the Young Modulus, I is the second moment of area of the cross section, k is the form factor describing the boundary conditions as fixed and free oscillating, $\rho$ is the density, A is the cross sectional area of the beam and L is the length of the filament or beam. Natural frequencies for complex structures with an uneven diameter can be calculated with finite element modelling methods.

A protrusion typically does not allow any significant movement within itself and therefore does have significant higher natural frequencies than a filament. A protrusion according to the present disclosure has a natural frequency of more than about 1200 Hz, in another embodiment more than about 2000 Hz and in yet another embodiment more than about 3000 Hz. In a further embodiment, the natural frequency of a protrusion is equal or larger than about 4000 Hz. Then its internal stiffness is so high that it would follow the motion of the carrier without noticeable internal flexing.

For example a cylindrical protrusion formed of nylon with a length of 5 mm, a diameter of 0.15 mm and a Young modulus of 3000 N/mm$^2$ treated as a cylindrical beam with one end fixed and the other end freely oscillating does have a (lowest) natural frequency of about 1400 Hz. At a length of 2.5 mm the lowest natural frequency would be about 5690 Hz. In an embodiment, the protrusions have a height (distance between free end and base) of maximally about 5.0 mm, in another embodiment less than about 4.0 mm, in another embodiment less than about 3.0 mm and in yet another embodiment less than about 2.0 mm. In one embodiment, the protrusion is formed of an elastomeric plastic material. Protrusions may be made of electrically isolating material and extend above the tongue cleaning electrode. Thus the protrusions when in use form a spacer between the tongue cleaning electrode and the user's tongue at least partly avoiding direct contact between the electrode and the tongue.

In a further embodiment, the electrode is implemented as a laminar electrode partly covered by a plurality of electrically isolating protrusions, for example, ribs, forming the structured surface of the mechanical tongue cleaning section. When viewed from above the ribs of the mechanical tongue cleaning section form a grid between which at a lower level the electrically conductive material of the electrode would be present.

In an embodiment, the tongue cleaning electrode includes a material selected from a group consisting of metal, in particular noble metal, for example, silver, stainless steel, an electrically conductive plastic or a combination thereof. In an embodiment, the tongue cleaning electrode itself may form the mechanical tongue cleaning section. This may for example be implemented by providing a rough electrically conductive surface having protrusions. In another embodiment, the electrode comprises a plurality of protrusions in the form of nubs. The nubs—when in use—point towards the user's tongue to provide places of high current density assisting to drive the ions as deep as possible into the pits and fissures between the papillae. In an embodiment, the protrusions, in particular the nubs have a height in a range from about 0.1 mm to about 2 mm measured from base to tip.

A nub is a protrusion whose height above the surrounding material is larger than or on the order of its widths or lengths. The nubs may have all kinds of different shapes. In particular the nubs may be cylindrical, conical, Gaussian or (hemi-)spheric. Besides nubs having a circular cross-section it is of course possible that the nubs have a triangular, rectangular or any other cross-sectional shape. The nubs may be arranged in a particular pattern or alternatively they could be arranged randomly. While the plurality of nubs may be formed of a single piece of electrically conductive material, for example, by punching a sheet of metal foil, the nubs need not necessarily be manufactured of a single piece, but could for example be arranged as a set of individual balls, which are separated from each other.

In an embodiment, the protrusions, in particular the nubs, have a widths in a range from about 0.1 mm to about 3 mm. In an embodiment, in which the nubs have a circular cross-section the widths of the nub is identical to its diameter. In a further embodiment the height of the protrusions, in particular the height of the nubs, is less than five times their diameter or width. In an embodiment, the area of the electrode covered by the nubs is in a range from between about 1% to about 50% of the overall area of the tongue cleaning electrode. In another embodiment, the area of the tongue cleaning electrode covered by the nubs is in a range from about 1 $mm^2$ to about 100 $mm^2$. The area of the tongue cleaning area may be in the range of between about 10 $mm^2$ and about 500 $mm^2$.

In an embodiment, the current density at the electrically conductive sections of the tongue cleaning electrode is higher than about 0.5 $\mu A/mm^2$ and in another embodiment less than about 60 $\mu A/mm^2$. For example for a current of 100 $\mu A$ the area of the electrically conductive sections of the electrode must have an area of less than about 200 $mm^2$. In a further embodiment, the high current density at the nubs is achieved when the nubs have a density of between about 5 $nubs/cm^2$ and about 50 $nubs/cm^2$ taking into account the overall area of the electrode.

The current density at the tip of each nub is even further enhanced when the electrically conductive nubs of the electrode are separated from each other by electrically isolating material sections. In an embodiment, this may be achieved by first forming an electrically conductive electrode comprising the nubs while in a second step the spacing between the nubs is partly filled with an electrically isolating material. The nubs may protrude over the electrically isolating material for providing contact points with the tongue. In an embodiment, the overall area of the electrically conductive sections of the electrode is smaller than about 200 $mm^2$ and in another embodiment equal to about 150 $mm^2$ or less.

In an embodiment the ratio between the area of the electrode covered by the nubs and the overall area of the electrode is equal or less than about 0.7, in another embodiment equal or less than about 0.3 and in another embodiment in a range from about 0.1 to about 0.3. In order to fit the dimensions of a common tongue the tongue cleaning electrode in an embodiment has a width in a range from about 0.2 cm to about 6 cm, in another embodiment in a range of between about 0.5 cm and about 3 cm. In an embodiment, the size of the tongue cleaning electrode is somewhat smaller than the back area of a replacement brush head and may thus have a width of about 0.4 mm to about 1.0 mm and a length (measured in longitudinal extension direction of the replacement brush head) of about 0.8 mm to about 2.5 mm.

In an embodiment, the head portion and the handle portion are detachably mounted to each other such that the head portion may be realized as a disposable exchange part. In order to achieve this it may be useful if the head portion and/or the handle portion comprise a mechanical connector for establishing a mechanical connection between the head portion and the handle portion and/or an electrical connector between the head portion and the handle portion for establishing an electrical connection. The electric current flowing through the user's body will be substantially reduced when a current flow is provided between the tongue cleaning electrode and the handle electrode, for example by a water film extending from the head section to the handle section. In order to prevent build up of an electrically conductive film between the two electrodes the head section and/or the handle section may comprise an annular protrusion acting as a tear-off edge for the film.

In an embodiment, the mouth cleaning device, in particular the head portion and/or the handle portion, are arranged such that they provide a vibrational motion of the head portion, in particular of the mechanical tongue cleaning section, where such is present. Such a vibrational motion could, for example, be caused by an ultrasound device, for example, a piezoelectric actuator, integrated into the head portion or into the handle portion, by driving the head portion with a linear drive or by including a motorized eccentric mass on a rotatable axis. In an embodiment, the vibrational motion provided in a tongue cleaning mode for cleaning the user's tongue has a frequency which is smaller than the frequency used for cleaning the user's teeth.

In an embodiment, the head portion includes an emitter for electromagnetic radiation, in particular a light emitting diode. This emitter may emit light in the visible range for illuminating the user's mouth. However, in another embodiment emission in other ranges of the electromagnetic spectrum may be considered.

An embodiment may further include cleaning elements (for example, bristles or elastomeric elements) provided in proximity of the tongue cleaning electrode to enhance the tongue cleaning performance.

FIG. 1 *a*) and b) show a first exemplary embodiment of a head portion 1 for a mouth cleaning device. The head portion 1 includes a front end 2, which is intended to be inserted into the user's oral cavity during operation, cleaning elements 6 form a brush portion 3, a tongue cleaning electrode 4, as well as a plurality of protrusions 5 in the form of plastic ribs that extend over the tongue cleaning electrode 4 forming a mechanical tongue cleaning section for scrubbing the tongue. In one embodiment, the brush 3 is a passive element which does not provide for any rotational or otherwise active motion of the cleaning elements 6. In one embodiment, cleaning elements 6 are bristles.

While the cleaning elements 6 of the brush 3 are facing into a first direction, i.e. when inserted into the user's oral cavity towards the user's teeth, the tongue cleaning electrode 4 as well as the mechanical tongue cleaning section 10 formed by the plastic ribs 5 face into a second direction being distinct over the direction the cleaning elements 6 are facing. Essentially, the tongue cleaning electrode 4 and the cleaning elements 6 are arranged on opposite sides of the head portion 2 so that they face into different directions such that they would not simultaneously get in contact with the tongue during a tongue cleaning operation (assuming that the tongue is kept in an essentially flat state). In this particular embodiment the brush 3 and the tongue cleaning electrode 4 and/or the plastic ribs 5 are arranged such that they are facing into opposite directions, i.e. when in use the brush may clean the masticatory surfaces of the teeth while simultaneously the tongue cleaning electrode 4 and/or the mechanical cleaning section formed by the ribs 5 could clean the user's tongue.

Figure 1B:
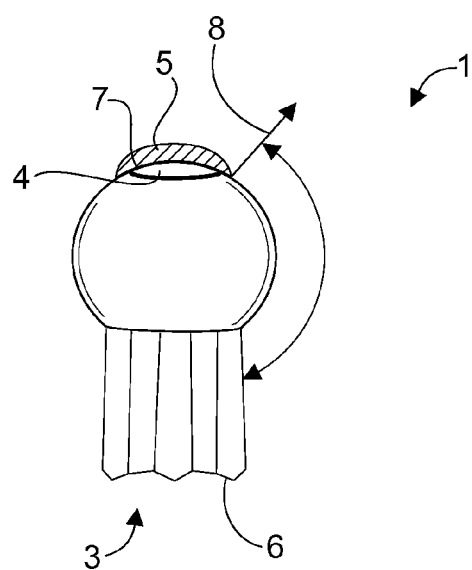

This situation is readily apparent from FIG. 1b) showing a schematic cross-sectional view of the head portion 1 of FIG. 1a). In the embodiment shown the tongue cleaning electrode 4 is a laminar electrode forming a section of the surface of the head portion 1 while the mechanical cleaning ribs 5 extend above the cleaning electrode in a more or less regular pattern. One advantage of the embodiment shown in FIGS. 1a) and 1b) is that when in use the electrode 4 will most probably not engage the tongue directly as the ribs 5 establish a distance between the top surface of the ribs 5 and the surface of the tongue cleaning electrode 4. The electric contact is nevertheless established by the liquid environment in the user's oral cavity.

The tongue cleaning electrode 4 has an electrode area 7 which is almost identical to the area of the extension of the tongue cleaning electrode 4 itself. However, it is reduced by the area covered by the plastic ribs 5. The electrode area 7 has at each point a surface normal 8 being perpendicular to the electrode area 7 of the tongue cleaning electrode 4. By this surface normal 8 it can be more clearly defined what it means that the brush 3 and the tongue cleaning electrode 4 as well as the mechanical cleaning section, i.e. the ribs 5, are facing into different directions. In the case depicted in FIGS. 1a) and 1b) each of the surface normals 8 on the surface area of the tongue cleaning electrode 4 do include an angle of at least about 135° with the cleaning elements realized as bristles 6 of the brush 3. In fact the angle included between the bristles 6 and surface normals 8 lies between about 135° and about 180°.

When in use as a tongue cleaner the mouth cleaning device is inserted into the user's oral cavity and the side of the head portion 1 on which the tongue cleaning electrode 4 is located is brought into contact with the user's tongue. In operation the side of the head portion 1 carrying the electrode 4 and the mechanical tongue cleaning section 10 is facing towards the user's tongue. The device 2 is moved such that the ribs 5 scrub over the surface of the tongue in order to mechanically remove part of the malodour producing bacteria. With respect to FIG. 4, in addition to the mechanical cleaning an electrophoretic cleaning is switched on by actuating the on/off-button of the handle portion 21. When switched on the energy source inside the handle portion 21 applies a voltage to the contact electrode 35 in the handle portion as well as to the tongue cleaning electrode 4 in the head portion 1 such that a potential difference exists between the both electrodes.

Assuming that the device 1 is inserted into the user's oral cavity by holding the handle portion 21 in the user's hand the current starts to flow through the user's body from the tongue cleaning electrode 4 to the contact electrode 35 in the handle portion 21 or vice versa as soon as the tongue cleaning electrode 4 is brought into contact with the tongue. For the present example it is assumed that the user has inserted a cleaning agent into the mouth containing positively charged ions before inserting the device 1 into the oral cavity. To achieve optimal results for driving the anti-bacterial ions into the pits and fissures between the papillae the voltage is applied to the two electrodes 4, 35 such that the tongue cleaning electrode 4 is positively charged against the contact electrode 35.

Figure 2:
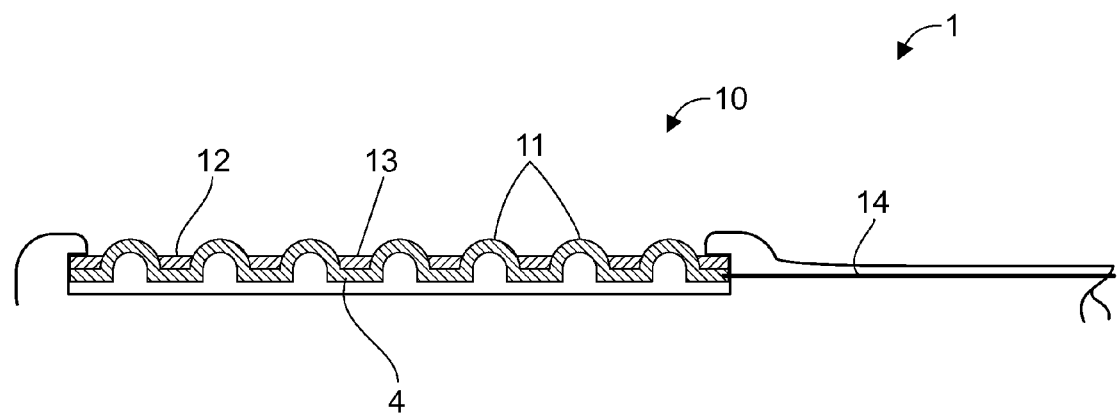
FIG. 2 is a section of a longitudinal cut through a tongue cleaning electrode in a head portion for a mouth cleaning device according to an exemplary embodiment.
Figure 3:
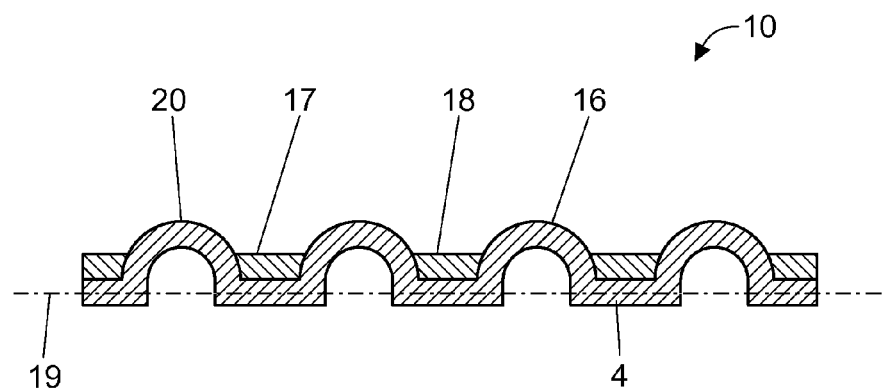
FIG. 3 is a section of a longitudinal cut through a tongue cleaning electrode in a head portion for a mouth cleaning device according to another exemplary embodiment.
Figure 8:
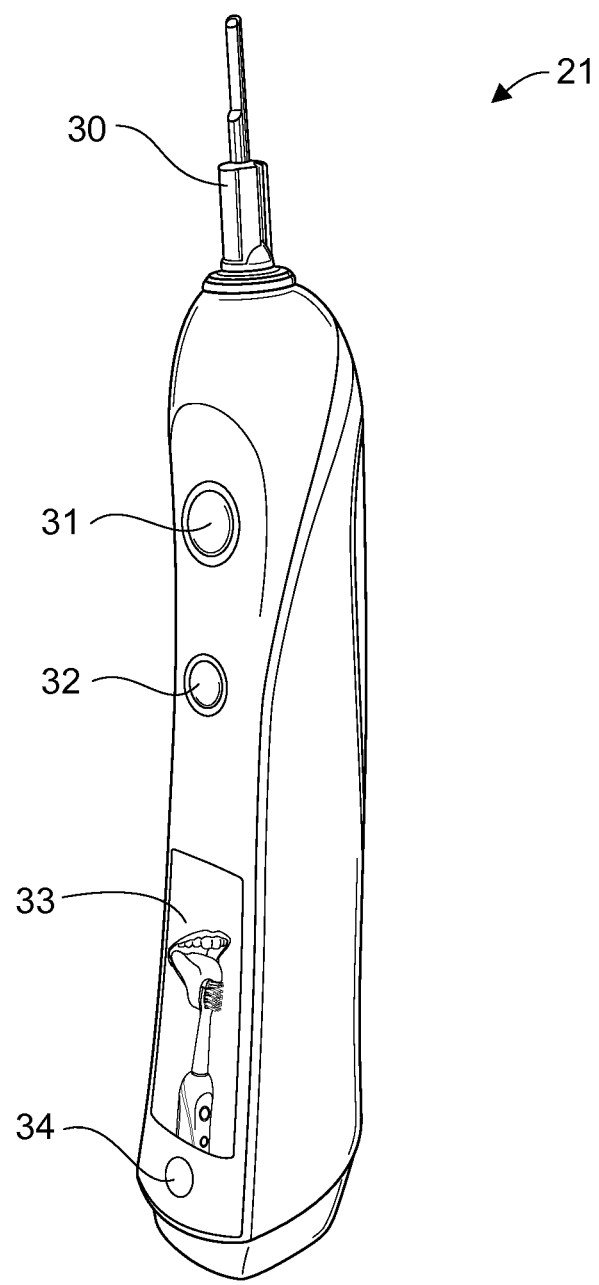
FIG. 8 shows a handle portion for a mouth cleaning device according to an embodiment.

FIGS. 2 and 3 show alternative arrangements of the tongue cleaning electrode and the mechanical tongue cleaning section. For the embodiment of FIG. 2, an alternative concept for implementing an integrated tongue cleaning electrode 4 and mechanical tongue cleaning section 10 has been chosen. Again, the areas over which the tongue cleaning electrode 4 extends and the area over which the mechanical tongue cleaning section 10 extends are spatially overlapping. The tongue cleaning electrode 4 is formed by a metal sheet which has been bent (for example, by stamping) in order to form a set of six protrusions realised as metallic ribs 11 protruding from the plane of the remaining laminar electrode structure. The orientation and arrangement of the electrode ribs 11 is comparable to the arrangement of the elastomeric ribs 5 of FIGS. 1a) and 1b). The space between the ribs 11 has been filled by an electrically isolating material 12, for example, a plastic material, (the isolating material 12 forms a layer over the electrode material). The isolating material 12 fills the spacing between the ribs 11 only partly such that the ribs 11 protrude over the surface level 13 of the isolating material 12 enabling an effective scrubbing when moving the head portion 1 of the device over the user's tongue. Also visible in FIG. 8 is the electric connection 14 connecting the electrode 9 with the current source in the handle portion of the device (not shown in FIG. 2).

The embodiment shown in FIG. 2 also makes it evident, what is meant by the term "electrode area". The term electrode area as used in the present disclosure denotes the overall area and shape of the electrode section, not only including the sections getting into electric contact with the user's tongue, like the ribs 11 in FIG. 2, but also including those sections underneath the isolating material 12. In particular if it comes to the question of shape and location of the electrode the electrode area is distinct from the surface area of the electrode. While the surface area also includes surface sections like the ribs 11 having surface normals facing into a variety of directions the electrode area of the electrode describes the overall shape of the electrode. In FIG. 2 the electrode area of the electrode is planar.

FIG. 3 shows a cross-sectional cut through an alternative embodiment of the tongue cleaning electrode 4. The tongue cleaning electrode 4 in this embodiment consists of a metal foil into which a plurality of protrusions in the form of nubs 16 have been stamped such that the nubs 16 protrude from the otherwise planar electrode 4. The spacing between the individual nubs 16 once again have been filled by an isolating material 17 (for example, by an elastomer) being electrically isolating. The nubs 16 further protrude above the surface level 18 of the isolating material 17. When in use an electric contact between the tongue cleaning electrode 4 and the user's tongue is only established by the tips of the individual nubs 16. Thereby the current density at the point of contact between the tongue and the tongue cleaning electrode 4 is enhanced leading to an improvement when cleaning the user's tongue.

In the embodiment depicted in FIG. 3, the electrode area of the tongue cleaning electrode 4 is indicated by the doted line 19. In particular the surface normals at each point of the electrode area are perpendicular to the dotted line but not perpendicular to the electrode surface 20 at each point of the tongue cleaning electrode 4 which at some locations differs substantially from the orientation of line 19, in particular at the nubs 16.

FIGS. 4 to 7 show embodiments of the present invention in which not only a tongue cleaning electrode 22 is provided but also a second electrode 23 facing into the same direction as the cleaning elements realized as bristles forming a brush 24. As FIGS. 4 to 7 are schematic sketches provided in order to describe the electric connectivity of the electrodes 22, 23, each of the electrodes 22, 23 and brushes 24 in the different figures have been denoted by the same reference numbers although they may be formed by different types of electrodes or bristles.

Figure 4:
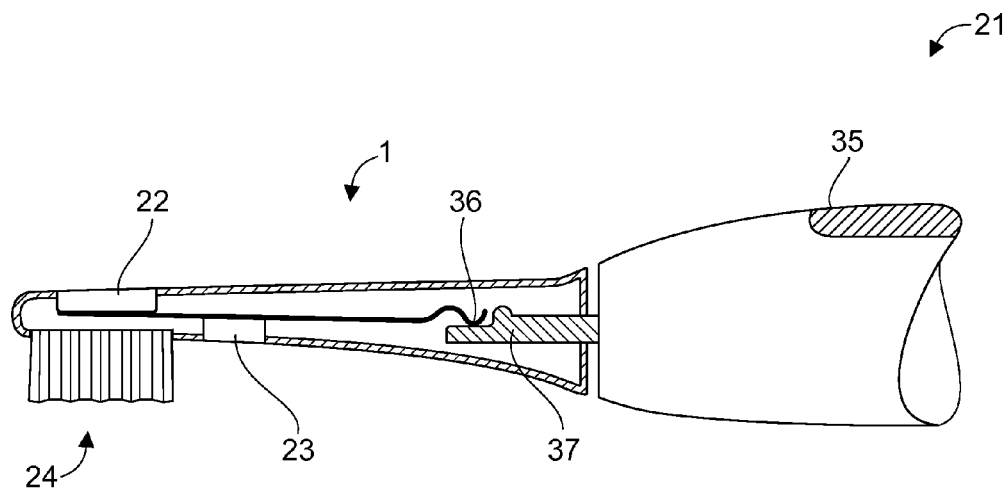
FIG. 4 shows a schematic depiction of an exemplary embodiment of a mouth cleaning device.
Figure 5:
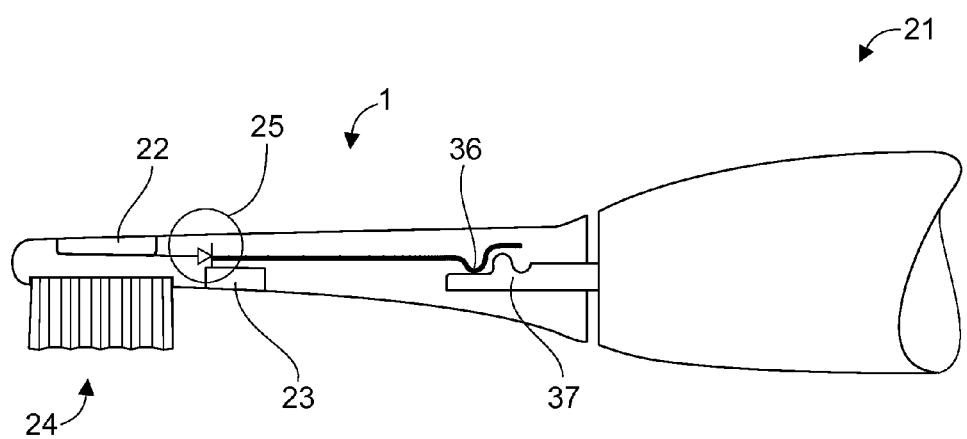
FIG. 5 shows a schematic depiction of another exemplary embodiment of a mouth cleaning device.
Figure 6:
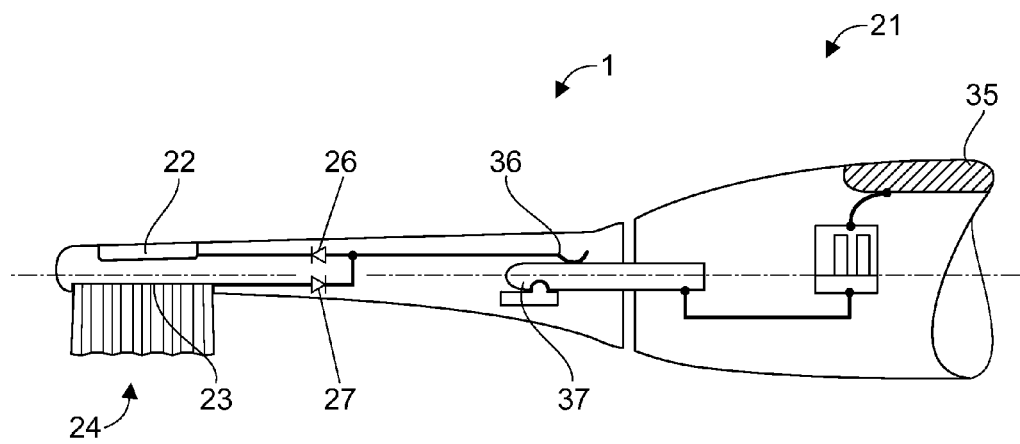
FIG. 6 shows a schematic depiction of a further exemplary embodiment of a mouth cleaning device.

While the tongue cleaning electrode 22 is used for cleaning the user's tongue as described with reference to FIGS. 1a) and 1b) the second electrode 23 will enable a current flow towards the user's teeth and gums while the brush 24 is used to clean the teeth. For all the embodiments depicted in FIGS. 4 to 6 it is assumed that the tongue cleaning electrode 22 is used in order to drive positively charged ions as an antibacterial agent towards the user's tongue and the second electrode 23 is used to drive negatively charged (for example, fluoride) ions towards the user's teeth, in particular to the enamel. In contrast, for the embodiment shown in FIG. 7 it is assumed that the polarity of the tongue cleaning electrode 22 is positive in order to drive negatively charged ions towards the user's tongue. Accordingly, the second electrode 23 facing towards the user's teeth has to be negatively charged in order to sufficiently transport negatively charged ions towards the teeth. FIG. 4 shows a simple embodiment in which both electrodes 22, 23 are simultaneously switched-on and provided with the same polarity. In order to switch between the two above described modes for cleaning the tongue or for cleaning the teeth the polarity of the two electrodes is switched with a corresponding switch element provided at the handle portion 21. Alternatively the circuit for driving the two electrodes 22, 23 could contain a diode 25 as shown in FIG. 5. This diode is arranged between the two electrodes 22, 23 such that the second electrode 23 is always switched on regardless of which polarity is chosen. However, the tongue cleaning electrode 22 is only provided with a positive charge and is switched off by the diode 25 when a negative polarity is chosen. FIG. 6 is a modification of the embodiment depicted in FIG. 5, the modification leading to a diode 26, 27 in front of each of the electrodes 22, 23. By this arrangement the tongue cleaning electrode 22 is only switched on when a positive polarity is chosen and the second electrode 23 for cleaning the user's teeth is only switched on when a negative polarity is chosen. Depending on polarity a current flows only through the tongue cleaning electrode or the second electrode. Instead of the diode different types of semiconductor elements such for example field effect transistors, thyristors, etc. could be used in order to provide a selective switching of the electrodes 22, 23. Alternatively the two electrodes 22, 23 may be coupled to a frequency dependent circuit. When the current is pulsating at a particular frequency, frequency filters can be applied in order to selectively drive the two electrodes 22, 23. By this kind of arrangement also more than two electrodes could be selectively operated.

Figure 7:
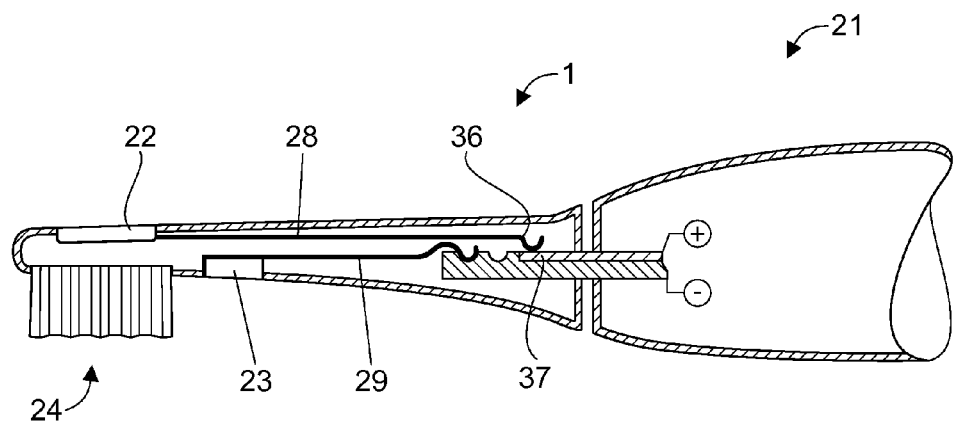
FIG. 7 shows a schematic depiction of an even further exemplary embodiment of a mouth cleaning device.

In the embodiment depicted in FIG. 6, the second electrode 23 is formed by conductive cleaning elements in order to provide the electrode as close to the teeth as possible. FIG. 7 shows an alternative embodiment in which the two electrodes 22, 23 have each been connected with a biasing line 28, 29, which can be selectively connected to the energy source.

In FIGS. 4 to 7 the electrical connecting elements 36, 37 of the head portion 1 and the handle portion 21 are shown, respectively. While the connecting element 36 of the head portion 1 is electrically connected to the tongue cleaning electrode 22, the connecting element 37 of the handle portion 37 is connected to the energy source. The connecting element 36 may be formed by a resilient connecting element, for example, a contact spring, that is arranged to engage with a complementary contact element at the handle portion 21. FIG. 8 is an example for a handle portion 21 of a mouth cleaning device containing not only the energy source for applying a current to the different electrodes, but also an electric motor driving a drive shaft 30 for providing a rotational motion of the brush, i.e. forming an electric tooth brush. The handle portion 21 in the depicted embodiment further comprises an on/off-button 31, a mode selection button 32, a display 33 for providing instructions on use of the device as well as information on the mode the device is currently operating in, and a light emitting diode 34 for indicating the charge condition of the energy source (for example, a rechargeable battery).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mouth cleaning device comprising:
   a handle portion having a contact electrode for enabling a current to flow into a user's hand in a use state;
   a head portion having teeth cleaning elements for cleaning teeth on a first face of the head portion and tongue cleaning elements on a face of the head portion opposing the first face; and
   a tongue cleaning electrode for enabling a current flow into a user's tongue and through the user's body in a use state;
   wherein the teeth cleaning elements and the tongue cleaning electrode are arranged on substantially opposing faces of the head portion, wherein the tongue cleaning electrode is located proximate to the tongue cleaning elements;
   and further comprising an energy source; wherein the energy source is electrically coupled to the contact electrode and to the tongue cleaning electrode such that in operation a current may flow from the contact electrode through a user's body to the tongue cleaning electrode.

2. The head portion according to claim 1, further comprising a second electrode arranged in proximity to the cleaning elements such that in a use state the cleaning elements and the second electrode simultaneously get in contact with the mouth region to be cleaned.

3. The head portion according to claim 2, wherein the second electrode is formed by electrically conductive cleaning elements.

4. The head portion according to claim 1, wherein the head portion includes a mechanical tongue cleaning section having at least one protrusion, the mechanical tongue cleaning section being arranged such that the tongue cleaning electrode and the mechanical tongue cleaning section simultaneously get in contact with a user's tongue in a use state.

5. The head portion according to claim 1, wherein the tongue cleaning electrode is a laminar electrode.

6. The head portion according to claim 4, wherein the area over which the mechanical tongue cleaning section extends at least partly spatially overlaps with the area over which the tongue cleaning electrode extends.

7. The head portion according claim 4, wherein the at least one protrusion is an arc shaped rib.

8. The head portion according to claim 4, wherein the at least one protrusion is formed of a plastic material.

9. The head portion according to claim 4, wherein the tongue cleaning electrode forms at least part of the mechanical tongue cleaning section.

10. The head portion according to claim 4 wherein the tongue cleaning electrode comprises a plurality of nubs.

11. The head portion according to claim 10, wherein the plurality of nubs are separated from each other by an electrically isolating material.

\* \* \* \* \*